United States Patent [19]
Vedamuthu et al.

[11] Patent Number: 5,919,695
[45] Date of Patent: Jul. 6, 1999

[54] METHOD AND CULTURE FOR INHIBITING UNDESIRED MICROORGANISMS WITH CULTURE OF *BACILLUS SUBTILIS*

[75] Inventors: Ebenezer R. Vedamuthu, Rochester, Minn.; Barbara J. Holler, Wauwatosa, Wis.; Petronella A. P. Vlegels, Huizen, Netherlands; Jeffrey K. Kondo, Rochester, Minn.; Declan MacFadden, Bussum, Netherlands; Larry L. McKay, St. Paul, Minn.; Daniel J. O'Sullivan, Minneapolis, Minn.; Purbita Ray, Oakdale, Minn.; Carla Gabriela Sanchez-Fernandez, Coyoacan, Mexico

[73] Assignees: Quest International, B.V., Huizerstraatweg, Netherlands; Regents of the University of Minnesota, Minneapolis, Minn.

[21] Appl. No.: 08/839,213

[22] Filed: Apr. 22, 1997

[51] Int. Cl.$^6$ .............................. C12N 1/12; A01N 63/00; A23C 9/12
[52] U.S. Cl. ................................. 435/252.5; 424/93.462; 426/61
[58] Field of Search ................... 435/252.5; 424/93.462; 426/61

[56] References Cited

U.S. PATENT DOCUMENTS

| | | | |
|---|---|---|---|
| 4,764,371 | 8/1988 | Pusey et al. .............................. | 424/93 |
| 4,931,398 | 6/1990 | Kimura ................. | 435/252.5 |
| 5,218,101 | 6/1993 | Hansen . | |
| 5,371,011 | 12/1994 | Bernier et al. ....................... | 435/252.4 |
| 5,516,682 | 5/1996 | Hansen . | |
| 5,667,779 | 9/1997 | Kubo .................................. | 424/93.462 |

OTHER PUBLICATIONS

Ulloa et al. Descripcion de dos especies nuvas de bacterias aissladas del pozol: Agrobacterium azotophilum y Achromobacter pozolis. Rev. lat–amer. Microbiol. 14: 15–24, 1972.

Sanchez–Fernandez et al. Microbial Antagonism of Agrobacterium azotophilum from Pozol, an Indigenous Fermented Food from Mexico. 1994 IFT Annual Meeting/Book of Abstracts p. 155.

Wacher et al, World J. Microbiol. Biochem. 9:269–274 (1993).

Nuraida et al, World J. Microbiol. Biochem. 11:567–571 (1995).

Herrera and Ulloa, Rev. Latin–Amer. Microbiol. 17:143–147 (1975).

Wilson, et al., SIM News 46:237–242 (1996).

Pusey et al., Plant Disease 72:622–626 (1988).

Gueldner et al., J. Agric. Food Chem. 36:366–370 (1988).

Asaka and Shoda, Appl. Environ. Microbiol. 62:4081–4085 (1996).

Handbook of Indigenous Fermented Foods, 2nd Ed., K.H.Steinkraus, Ed., Marcel Dekker, Inc., New York, New York pp. 252–259 (1996).

Sanchez–Fernandez, C.G., "Microbial Antagonism of *Agrobacterium Azotophilum* from Pozol, A Traditional Fermented Food from Mexico," Master's thesis, University of Minnesota (1994).

De Smedt, J., et al., Int'l J. Systematic Bacteriol., 27:222–240 (1977).

Ulloa, M., et al., Fermented Corn Products of Medico, in C.W. Hesseltine et al., Ed., Indigenous Fermented Food of Non–Western Origin, J. Cramer, Publishers, Berlin pp. 151–165 (1986).

*Primary Examiner*—Sandra E. Saucier
*Assistant Examiner*—Vera Afremova
*Attorney, Agent, or Firm*—Ian C. McLeod

[57] ABSTRACT

An atypical *Bacillus subtilis* strain NRRL B-21974 from Pozol, a Mexican beverage, is used in controlling molds and other spoilage flora in various materials, particularly foods including dough, tortillas, moist grains and cheese. The *Bacillus subtilis* strain can be used in living or non-living form in the materials. The materials can include packaging for foods.

16 Claims, No Drawings

_5,919,695_

METHOD AND CULTURE FOR INHIBITING UNDESIRED MICROORGANISMS WITH CULTURE OF BACILLUS SUBTILIS

BACKGROUND OF THE INVENTION (1) Summary of the Invention

The present invention relates to a unique atypical culture of *Bacillus subtilis* which is used to preserve materials containing, or exposed, to undesired microorganisms. In particular, the present invention relates to a culture isolated from Pozol which inhibits a wide variety of gram-positive and gram-negative bacterium, yeasts and molds.

(2) Description of Related Art

Foods and feeds are particularly labile to microbial deterioration, and can serve as vehicles for transmission of pathogens, food-borne infections and intoxications. The microorganisms involved include bacteria, yeasts, molds and viruses. Some examples of food and feed-borne pathogens are for instance *Staphylococcus aureus,* Salmonella spp., Clostridium spp., *Listeria monocytogenes,* Yersinia spp., Vibrio spp., *Escherichia coli* serotype O157:H7, and Shigella spp. Enterotoxins produced by staphylococci, clostridia, and mycotoxins secreted by molds are also transmitted through foods and feeds.

Several different approaches are used to prevent microbial deterioration of foods and feeds, and transmission of microbial pathogens and/or their toxins through foods and feeds. Most of these strategies include using adequate processing methods and avoiding and preventing post-process contamination. Supplementing these steps are the use of preservatives, packaging techniques, such as vacuum shrinking films, and modified atmosphere packaging. Recently there has been an increased interest in searching for "natural inhibitors" of unwanted flora in foods and feeds. These inhibitors have included using antagonistic "safe" microorganisms such as lactic acid bacteria, microbial metabolites, such as organic acids, bacteriocins, and certain naturally derived components like spice and plant extracts.

The health promoting and antibacterial properties of a fermented Mexican drink, Pozol, have been recognized by the Mayan civilization for centuries. Pozol is made by dissolving fermented nixtamalized corn (maize) flour dough or masa in water. Only recently, have there been careful microbiological studies on this fermented native drink. The microflora of Pozol is quite complex. Wacher et al. (World J. Microbiol. Biochem. 9:269–274 (1993)) and Nuraida et al. (World J. Microbiol. Biochem. 11:567:571 (1995)) reported that the predominant microflora of Pozol consisted of lactic acid bacteria (lactobacilli, lactococci, and leuconostocs), aerobic catalase-positive mesophiles, members of the Enterobacteriaceae family, yeasts (predominantly *Geotrichum candidum*) and molds.

Earlier studies by Mexican researchers showed that Pozol contained *Agrobacterium azotophilum* (Ulloa and Herrera. Rev. Latin-amer. Microbiol. 14:15–24 (1972)), which showed a wide antibacterial activity (Herrera and Ulloa. Rev. Latin-amer. Microbiol. 17:143–147 (1975)). The *Agrobacterium azotophilum* isolate was a Gram-negative, non-spore forming, coccoid-bacillus, which was capsulated, and motile (Ulloa and Herrera. Rev. Latin-amer. Microbiol. 14:15–24 (1972)). They also noted that the bacterium inhibited the growth of several Gram-positive and Gram-negative bacteria, yeasts and molds. Later studies by others also attributed the antimicrobial properties of Pozol to isolates similar to *Agrobacterium azotophilum* (Sanchez-Fernandez and McKay. Abst. IFT Annu. Meet. Food Expo (1994)). This was a misidentification of the bacterium involved and in fact it is the strain of the present invention.

There are previous reports in the literature describing the inhibitory properties of *Bacillus subtilis* strains isolated from other habitats. Wilson et al., (SIM News 46:237–242 (1996)) referred to a *Bacillus subtilis* isolate B-3, that was effective in controlling brown rot of peaches, and was tested successfully on a semi-commercial basis in packing houses (Pusey et al., Plant Disease 72:622–626 (1988)). This strain was patented in 1984 (Pusey, L., and Wilson, C. L., U.S. Pat. No. 4,764,371). The principal agent involved in the antagonistic activity of the strain B-3 against brown rot pathogen of peaches, was found to be an antibiotic, iturin, secreted by the Bacillus (Gueldner et al., J. Agric. Food Chem. 36:366–370 (1988)). Asaka and Shoda (Appl. Environ. Microbiol. 62:4081–4085 (1996)) described the use of a strain of *Bacillus subtilis,* designated RB14, for controlling damping-off in tomato seedlings caused by a mold. This strain was shown to be active against several phytopathogens in in vitro studies. This strain produced two antibiotics, iturin A and surfactin, which were found in cell-free culture supernatants. Asaka and Shoda also cited other investigations, where *Bacillus subtilis* strains have been used to control phytopathogens in plant growth studies. No application studies on the use of microorganisms from Pozol to control unwanted flora in foods or feeds or other systems have been reported. Other U.S. patents of interest are U.S. Pat. Nos. 5,218,101 to Hansen and 5,516,682 to Hansen which relate to mutant subtilins.

DESCRIPTION OF PREFERRED EMBODIMENTS

The present invention relates to a method for inhibiting undesirable microorganisms in a material containing or exposed to the microorganisms which comprises:

exposing the material to an inhibitor of the undesired microorganisms from a pure culture of a *Bacillus subtilis* deposited as NRRL B-21974 so that the undesired microorganisms in the material are inhibited. Preferably the material to be protected is a food or a material in contact with a food. The food can be for any animal, particularly mammals.

The present invention also relates to an isolated pure culture of *Bacillus subtilis* deposited as NRRL B-21974.

The culture was deposited with the Northern Regional Research Laboratory (NRRL) 1815 N. University Street, Peoria, Ill. 61604 on Apr. 11, 1998 as NRRL B-21974 under the Budapest Treaty. The culture will be available to all who request it upon issuance of a patent.

The culture of the *Bacillus subtilis* NRRL B-21974 can be living or non-living. If living, it can be frozen or lyophilized or otherwise dried for preservation. The inhibition is produced by a component of the *Bacillus subtilis* and thus it can be non-living. It can be sonicated or otherwise disrupted for preservation prior to use. All of these variations are known to those skilled in the art.

Preferably the culture of living cells contains between about $10^3$ and $10^{12}$ cell forming units (cfu) per ml or gram. Most preferred is $10^6$ to $10^9$ cfu per ml.

The material being preserved preferably contains between about $10^2$ and $10^9$ cfu per ml or gram. The amount selected depends upon the material and the undesirable microorganisms which are present. If the culture is non-living, an amount of inhibitory cellular material is used for inhibition.

The culture material can be incorporated into a bulking agent for distribution into the materials. Most conveniently the culture material is incorporated into a dry edible particulate material, such as flour, non-fat dry milk, salt, or pepper, which can be incorporated into the food.

The following Example 1 shows the growth and preservation of the *Bacillus subtilis*. In the following Examples 2 to 7, application of the *Bacillus subtilis* Pozol isolate in food systems to inhibit unwanted flora is described. A broad application of the isolate to control undesirable microflora in various food and feed systems is evident from the Examples described hereunder.

EXAMPLE 1

The isolate from Pozol that exhibited the wide spectrum of inhibition is a Gram-positive, aerobic, spore-forming rod. The spores are sub-terminal to terminal, and the sporangia are swollen at the position of the endospore. Active, young cultures exhibit good motility. The rods are medium-sized, and usually occur as single cells. Older cells exhibit Gram-variable reaction. Extensive sporulation is observed on solid media, and very little or no sporulation occurs in broth cultures. Broth cultures fortified with minerals and starch, incubated for long periods (72 hours or greater) on a shaker show a fair amount of sporulation. Biochemical data indicate that the organism is an atypical strain of *Bacillus subtilis*. One of the unique properties of the organism is its ability to grow on a nitrogen-free medium, but containing a carbon source. The organism survives well in dough systems without any supplementation with exogenous sugar or nitrogen compounds. The biochemical characteristics of the organism as determined by the API system is given in Tables 1 and 2.

TABLE 1

Biochemical reactions of Pozol isolate as determined by API 50 CHB sugar fermentation system

| Sugar | Fermentation | Sugar | Fermentation |
|---|---|---|---|
| Control | − | Esculin | ++++ |
| Glycerol | ++++ | Salicin | +++ |
| Erythritol | − | Cellobiose | ++++ |
| D-Arabinose | − | Maltose | ++++ |
| L-Arabinose | ++++ | Lactose | ++++ |
| Ribose | ++++ | Melibiose | +++ |
| D-Xylose | +++ | Sucrose | ++++ |
| L-Xylose | − | Trehalose | ++++ |
| Adonitol | − | Inuline | − |
| β-Methyl-C-Xyloside | − | Melezitose | − |
| Galactose | − | Raffinose | ++++ |
| Glucose | ++++ | Starch | +++ |
| Fructose | ++++ | Glycogen | ++++ |
| Mannose | ++++ | Xylitol | + |
| Sorbose | − | β-Gentiobiose | + |
| Rhamnose | − | D-Turanose | ++++ |
| Dulcitol | − | D-Lyxose | − |
| Inositol | ++++ | D-Tagatose | − |
| Mannitol | ++++ | D-Fucose | − |
| Sorbitol | ++++ | L-Fucose | − |
| α-Methyl-D-Mannoside | − | D-Arabitol | − |
| α-Methyl-D-Glucoside | +++ | L-Arabitol | − |
| N-Acetyl-Glucosamine | − | Gluconate | − |
| Amygdalin | +++ | 2-Keto-gluconate | − |
| Arbutin | +++ | 5-Keto-gluconate | − |

++++ full acidification (yellow)
+++ less acidification (less intense yellow)
++ minor acidification (orange/yellow)
+ slight acidification (red/orange)
− no acidification

TABLE 2

Biochemical reactions of Pozol isolate as determined by API 20E

| | 24 h | 48 h |
|---|---|---|
| Ortho-Nitrophenyl N-Acetyl-α-D-Galactosaminide Hydrolysis | − | − |
| Aginine Dihydrolase | + | + |
| Lysine Decarboxylase | − | + |
| Ornithine Decarboxylase | +/− | + |
| Citrate Utilization | − | − |
| Hydrogen Sulfide | − | − |
| Urease | + | + |
| Tryptophane Deaminase | a | − |
| Indole from Tryptophane | a | − |
| Voges-Proskauer | a | + |
| Gelatin Liquefaction | + | + |
| Glucose | − | − |
| Nitrate Reduction | a | + |

[a] reading after addition chemicals to cupule after 48 h.
+ positive reaction after 24 hours or 48 hours at 37°, according color change necessary for positive result as listed in the instructions.
− negative reaction after 24 hours and 48 hours.
+/− slight positive reaction.

The inhibitory spectrum of the bacterium against some of the spoilage flora in foods is given in Table 3.

TABLE 3

Inhibitory spectrum of the Pozol isolate against certain common spoilage and pathogenic microflora in foods.[a]

| Microorganism | Strain No./Designation[b] | Inhibition[c] |
|---|---|---|
| I. BACTERIA | | |
| Gram - positive | | |
| Enterococcus faecium | QRHy | +++ |
| Lactobacillus spp.[d] | QR196 | +++ |
| Lactobacillus spp.[d] | QR396 | +++ |
| Listeria monocytogenes | QRLMO36 | ++ |
| Listeria monocytogenes | ATCC43256 | +++ |
| Staphylococcus aureus | ATCC10390 | − |
| Gram - negative | | |
| Escherichia coli | ATCC12955 | +++ |
| Pseudomonas aeruginosa | ATCC10145 | +++ |
| Pseudomonas fluorescens | QR22 | +++ |
| Salmonella enteritidis | ATCC13076 | +++ |
| II. YEASTS | | |
| Candida glabrata | ATCC2001 | +++ |
| Debaryomyces polymorphus | ATCC20280 | +++ |
| Rhodotorula mucilaginosa var. mucilaginosa | ATCC9449 | +++ |
| Saccharomyces spp.[e] | QR96 | +++ |
| III. MOLDS | | |
| Aspergillus flavus | QN25581 | + |
| Fusarium avenaceum | QN25565 | + |
| Fusarium culmorum | QN25656 | ++ |
| Fusarium oxysporum | ATCC48112 | +++ |
| Geotrichum candidum | ATCC34614 | + |
| Penicillium spp.[f] | QR15 | +++ |

[a] Determined by deferred agar overlay assay.
[b] ATCC - American Type Culture Collection
QN - Quest, Naarden Culture Collection
QR - Quest, Rochester Culture Collection
[c] - No inhibition.
+ - Zone of inhibition <5 mm.

TABLE 3-continued

Inhibitory spectrum of the Pozol isolate
against certain common spoilage and pathogenic
microflora in foods.[a]

| Microorganism | Strain No./Designation[b] | Inhibition[c] |
| --- | --- | --- |

++ - Zone of inhibition >5 mm but <10 mm.
+++ - Zone of inhibition >10 mm.
[d]Isolates from spoiled processed meats.
[e]Isolate from sour dough bread starter.
[f]Isolate from moldy tortilla.

The organism is active against Gram-negative and Gram-positive bacteria, molds and yeasts, which are common spoilage flora in foods. Many Gram-negative bacteria such as Salmonella, Shigella, certain serological types of Escherichia, and the like are food-borne pathogens.

To insure the uniformity of inoculum used in the following Examples, a frozen concentrate of the strain was made in the laboratory using a 1.0 liter fermentor. The strain was grown in a medium consisting of the following: NZ-Amine EKC—0.5%; Amberex 1003 yeast extract—0.5%; dextrose—2.0%; mannitol—1.0%; sodium citrate—0.1%; magnesium sulfate—0.1%; dipotassium hydrogen phosphate—0.2%; and calcium chloride—0.1%; tap water—1.0 liter. The medium was sterilized in-place in the fermentor at 121° C. for 15 minutes. The pH after sterilization was 6.2. The medium was tempered to 30° C., and the initial pH was adjusted to 6.5. The fermentor was inoculated at 1.0%. The growth of the strain in the fermentor was carried out at 30° C., with agitation set at 250 RPM and the pH control set at 5.0. After 24 hours of growth, the cells were harvested by centrifugation, and the cell pellet was resuspended in the supernatant to give 20X concentration. Ten percent (v/v) of glycerol was added as cryoprotectant, and the cell concentrate was distributed in 5.0 ml volumes into sterile plastic tubes and were frozen and held at −80° C. The count of the bacteria in the frozen concentrate was $1.9 \times 10^9$ cfu/ml as determined on Tryptone Soy Agar fortified with 1.0% mannitol.

EXAMPLE 2

Moist grains and cereals are prone to spoilage through mold growth, which in many cases lead to the elaboration of mycotoxins in the molding grains, cereals, and feeds. If mold growth could be retarded or prevented in stored grains or cereals, a lot of wastage could be avoided. The efficacy of the *Bacillus subtilis* strain in inhibiting mold growth was tested in a moist grain system using barley grains.

Barley grains were purchased from a local store. The mold count of the grain was determined. The grain was thoroughly mixed, and a representative 11.0 g sample was added to a 99.0 ml dilution blank, mixed well, and 0.1 ml aliquots from the dilution bottle were spread-plated on 10 plates of Acidified Potato Dextrose Agar (Difco, Detroit, Mich.). After incubation at 28° C. for 4 days, the mold colonies formed on the 10 plates were counted and reported as cfu/g. The count of molds/g of the barley grains were 6 molds (cfu)/g.

One hundred grams of barley grains were weighed out into a shallow rectangular porcelain dish. Using a graduated cylinder, 50 ml of tap water was measured and used to moisten the barley evenly. This was done by stirring the grain thoroughly with a spatula. Another dish was prepared identically. The excess moisture in the dishes was carefully drained out. The dishes were labeled A and B. To dish A, 10 ml of sterile Tryptone Soy Broth containing 1% mannitol (TSM broth) was added and mixed well to get homogeneity. To the dish labeled B, 10 ml of $1 \times 10^{-4}$ dilution of the concentrate of the *Bacillus subtilis* strain made with sterile TSM broth was added, and mixed to get uniform distribution. This delivered approximately $1 \times 10^4$ CFU/g of barley. The dishes were covered tightly with plastic wrap, and placed in an incubator held at 28° C. The dishes were examined every day until mold growth was noticed.

For the first three days no visible mold growth was observed. On the fourth day, the dish to which sterile TSM broth was added was totally covered with mold mycelia all over the surface. The dish to which the *Bacillus subtilis* strain diluted in TSM broth was added had only three isolated spots of mold on the entire surface. There was definite inhibition of indigenous mold flora in the moistened barley, when the *Bacillus subtilis* strain was present. The experiment was repeated with duplicate dishes for the control and experimental barley grains, using different inoculation rates of the Pozol isolate. Addition of the *Bacillus subtilis* strain inhibited mold development on moistened barley grains. The results are summarized in Tables 4 and 5.

TABLE 4

Effect of adding *Bacillus subtilis* strain on molding of barley grains.

| Treatment[a] | Days at 28° C. | Smell | Presence of mold |
| --- | --- | --- | --- |
| Dish A | 0 | Normal | None |
| Dish B | 0 | Normal | None |
| Dish A | 1 | Normal | None |
| Dish B | 1 | Normal | None |
| Dish A | 2 | Normal | None |
| Dish B | 2 | Normal | None |
| Dish A | 3 | Normal | None |
| Dish B | 3 | Normal | None |
| Dish A | 4 | Musty, moldy | +++++[b] |
| Dish B | 4 | Moldy | +[c] |

[a]Control barley with sterile TSM broth added (Dish A) Experimental barley with $1 \times 10^4$ CFU/g of *Bacillus subtilis* strain (Dish B)
[b]Entire surface of the barley was covered with mold mycelia
[c]Three isolated patches of mold mycelia

TABLE 5

Effect of adding *Bacillus subtilis* strain on molding of barley grains

| Treatment[a] | Mold development[b,c] | | | | |
| --- | --- | --- | --- | --- | --- |
| | Day 0 | Day 1 | Day 4 | Day 5 | Day 6 |
| 1A | None | None | +++ | ++++ | ++++(+) |
| 1B | None | None | +++ | ++++ | ++++(+) |
| 2A | None | None | + | + | + |
| 2B | None | None | + | ++ | ++ |
| 3A | None | None | None | ++ | ++ |
| 3B | None | None | None | None | None |
| 4 | None | None | None | ++ | ++ |

[a]1A - Uninoculated control
1B - Duplicate of uninoculated control
2A - With $1 \times 10^7$ *Bacillus subtilis*/g of barley
2B - Duplicate of 2A
3A - With $1 \times 10^6$ *Bacillus subtilis*/g of barley
3B - Duplicate of 3A
4 - With $1 \times 10^4$ *Bacillus subtilis*/g of barley
[b]No observations were made on days 2 and 3. Experiment terminated on day 6
[c]+ A few isolated spots of mold TABLE 5-continued Effect of adding *Bacillus subtilis* strain on molding of barley grains

| Treatment[a] | Mold development[b,c] | | | | |
|---|---|---|---|---|---|
| | Day 0 | Day 1 | Day 4 | Day 5 | Day 6 |

++ About 15–20% of the surface covered with mold
+++ >50% of the surface covered with mold
++++ >75% of the surface covered with mold
++++(+) >80% of the surface covered with thick mat of mycelia
None No mold development These results indicate that the *Bacillus subtilis* strain in the form of a spray can be used to control mold growth in grains in general, and underground crops like peanuts. Such a treatment can be used to prevent mycotoxin formation in various cereal grains, and peanuts. Similar treatment can be used to control mold development, and accompanying defects like "gushing", during steeping and malting of cereals used in brewing industries.

EXAMPLE 3

The nixtamalized corn flour made into dough is not only used for making Pozol, but also for making tortillas. One of the major problems in the distribution and marketing of tortillas is the appearance of mold spots and patches of mold discoloration on packaged tortillas. In this Example, the efficacy of adding the *Bacillus subtilis* strain to the corn dough in controlling mold growth in packaged tortillas is demonstrated. Additionally, the efficacy of adding the *Bacillus subtilis* strain in controlling the spoilage, and molding of stored dough is also demonstrated.

Nixtamalized, vitamin fortified corn flour sold by Quaker Oats Company (Chicago, Ill.) under the registered trademark QUAKER MASA HARINA DE MAIZE™ was purchased from a local grocery store. Masa dough was made according to the instructions on the package. Using 3 cup measures of Masa flour and mixing in 2¼, cup measures of warm tap water, about 800 g of Masa dough was made. This was divided into two portions of 400 g each, and placed in two separate beakers, labeled A and B. To the dough in beaker A, 4.0 ml of sterile TSM broth was added. To beaker B, 4.0 ml of a $10^{-3}$ dilution of the cell concentrate of the *Bacillus subtilis* strain was added. The diluent used was sterile TSM broth. Both samples were thoroughly mixed avoiding cross-contamination. The diluted culture added to the dough would deliver $1\times10^4$ organisms/g of dough. After removing about 50 g of dough from each beaker for tortilla making, the beakers were covered with aluminum foil, and placed in a 28° C. incubator. Two tortillas from each sample were made using an electric tortilla-maker (Vitantonio Mfg. Co., East Lake Ohio 44094). Each tortilla was placed separately in a ZIPLOC bag, sealed, labeled for identity, and placed in an incubator at 28° C.

Every day, the dough samples and corresponding tortillas made from the uninoculated and inoculated dough were examined for the presence of mold growth by macroscopic observation for spots or patches of mycelial growth. Total microbial counts were also made on the dough using TSM agar. The smell (olfactory response) of the dough samples and the corresponding tortillas were also recorded.

For the first two days no mold growth was seen in any of the dough samples. After the first day, the uninoculated and inoculated dough samples were found to have slightly sour smell. On the second day, the uninoculated dough had a strong sour odor, while the inoculated sample did not differ in smell from the previous day. On the third day, relatively extensive white mycelial growth was seen on the uninoculated sample, while the inoculated dough had limited, localized mold spots. The control dough retained the strong sour smell; the inoculated dough only had a slightly sour odor.

On the second day, the uninoculated dough sample had slimy patches on the surface, while the inoculated sample appeared normal. The plate counts assayed on the dough after 3 days showed that on the control sample there was a confluent growth of contaminants at $10^{-4}$ dilution on the third day. On the same day, and at the same dilution, the inoculated sample had much thinner growth of contaminants (clearly discernable individual colonies could be seen). The results are summarized in Table 6.

TABLE 6

Effect of adding *Bacillus subtilis* on the shelf-life and mold development on masa dough.

| Treatment[a] | Days at 28° C. | Appearance | Odor | Mold | Bacterial count (CFU/g)[b] |
|---|---|---|---|---|---|
| Control | 0 | Normal | Normal | None | $3.6 \times 10^4$ |
| Experimental | 0 | Normal | Normal | None | $1.9 \times 10^4$ |
| Control | 1 | Moist | Sl.sour | None | ND[c] |
| Experimental | 1 | Moist | Sl.sour | None | ND |
| Control | 2 | Slimy | Sour | None | $1.8 \times 10^{9d}$ |
| Experimental | 2 | Moist | Sl.sour | None | $1.8 \times 20^{9d}$ |
| Control | 3 | Slimy | Sour | +++[e] | TNTC[f] |
| Experimental | 3 | Moist | Sl.sour | +[e] | TNTC[f] |
| Control | 4 | —[g] | Moldy | ++++[e] | TNTC[f] |
| Experimental | 4 | —[g] | Sl.sour | ++[e] | TNTC[f] |

[a]Control - Uninoculated dough
Experimental - Inoculated with $1 \times 10^4$ *Bacillus subtilis*/g of dough
[b]Count made on TSM agar
[c]Not determined
[d]Counts made in parallel on Minimal agar showed $6.1 \times 10^8$ CFU/g for control and $1.5 \times 10^6$ CFU/g for the experimental sample
[e]+ Small isolated spots of mold mycelia
++ Isolated patches of mold mycelia
+++ Confluent mat of mycelia
++++ Extensive growth of mycelia
[f]TNTC - Too numerous to count. Confluent growth of bacteria at $1 \times 10^{-4}$ dilution. Control sample was heavily contaminated by yellow pigmented bacteria. Yellow contaminants were absent on the experimental dough.
[g]Appearance could not be determined because the surface was covered by mold growth.

Tortillas made from the uninoculated and inoculated dough were also examined daily for mold growth and for the development of off-odors. For the first two days, no molds were seen in any of the tortillas. On the fourth day, the control tortillas showed mold spots (4 spots on two tortillas); by the sixth day both the control tortillas were totally covered with mold. In contrast no mold patches were seen on the tortillas made from inoculated dough until the fifth day. On the sixth day, only one spot was seen on one of the tortillas; no increase of mold growth was seen on further incubation. Tortillas made with control dough developed off-odor after the fourth day. Tortillas made from inoculated dough was judged to be slightly off in odor on the fifth day (Table 7).

TABLE 7

Effect of adding *Bacillus subtilis* strain to masa dough on mold development in tortillas made from the dough.

| Days at 28° C. | Control[a] Odor | Control[a] Mold | Experimental[b] Odor | Experimental[b] Mold |
|---|---|---|---|---|
| 0 | Normal | None | Normal | None |
| 1 | Normal | None | Normal | None |
| 2 | Normal | None | Normal | None |
| 3 | Normal | 1 spot/2[c] | Normal | None |
| 4 | Sl. Sour[d] | 4 spots/2 | Sl. Sour | None |
| 5 | Sour | 5 spots/2 | Sl. Sour | None |
| 6 | Sour | +++++[e] | Sour | 1 spot/2 |
| 7 | Off | +++++ | Off | 1 spot/2 |
| 8 | Off | +++++ | Off | 1 spot/2 |

[a]Tortillas made from uninoculated dough.
[b]Tortillas made from inoculated dough.
[c]Indicates number of mold spots on two tortillas.
[d]Sl. Sour - slightly sour
[e]Tortilla completely covered with mold growth.

In a repeat trial, dough that was not inoculated with the *Bacillus subtilis* isolate developed mold growth on the second day, which on the third day covered the surface completely. The odor of the dough was also found to be off by the second day. The inoculated dough had no mold growth for the first two days, and had a few isolated spots of mycelial growth on the third day.

These observations on two trials showed that by inoculating masa dough with the *Bacillus subtilis* strain, the shelf-life of the dough and tortillas made from the dough can be extended. Similar treatment of various dough products, used in the production of various breads, indigenous flat breads, bakery goods, and pastas, can be used to extend shelf-life.

EXAMPLE 4

To further determine the amount of inoculated dough needed in a masa dough mix to inhibit contaminants, and development of off odors, dough mixes containing different levels of inoculated dough (inoculated with 1×10$^4$ cells of *Bacillus subtilis* strain/g of dough and incubated for 48 hours at 28° C.) were made. The levels of inoculated dough used were 0%, 25%, 50% and 100%. The dough samples were placed in clean glass beakers, covered with aluminum foil, and placed in an incubator at 28° C. The samples were examined every day for mold growth and off-odors.

The odor of the samples containing different proportions of inoculated dough were scored to be sour after the first day. The control dough retained the normal flavor. After the second day, the control sample was very sour, which progressed to an off-odor by the third day. On the third day, the sample containing 25% inoculated dough was also considered to have an off odor. Samples containing higher levels of inoculated dough, namely, 50% and 100% were found to be devoid of off odor.

For the first three days, no mold growth was observed on any of the samples. After the third day, the control sample was totally covered with mold. There was limited, localized mold spots on the sample containing 25% inoculated dough. No mold growth was noted on samples containing 50% and 100% inoculated dough (Table 8).

TABLE 8

Molding of masa dough containing different levels of cultured dough[a].

| Days at 28° C. | 0 Odor | 0 Mold | 25 Odor | 25 Mold | 50 Odor | 50 Mold | 100 Odor | 100 Mold |
|---|---|---|---|---|---|---|---|---|
| 0 | Normal | none | Normal | None | Sl. Sour[b] | None | Sour | None |
| 1 | Sl. Sour | None | Sl. Sour | None | Sour | None | Sour | None |
| 2 | Very Sour | None | Sour | None | Sour | None | Off | None |
| 3 | Off | ++++[c] | Off | ++ | Off | None | Off | None |
| 4 | Off | +++++ | Off | ++ | Off | None | Off | + |
| 5 | Off | +++++ | Off | +++ | Off | None | Off | + |

[a]Masa dough was inoculated with 1 × 10$^4$ *Bacillus subtilis*/gram of dough and cultured for 48 hours at 28° C.
[b]Sl. Sour - slightly sour.
[c]None - no mold development
+ - one or two isolated spots.
++ - a few patches of mold.
++++ - >80% of the surface covered by mold.
+++++ - entire surface covered with mold.

From the foregoing observations, it is apparent that the use of inoculated dough would aid in controlling mold growth and offer shell-life extension in dough products.

EXAMPLE 5

In an additional trial, masa dough inoculated with the *Bacillus subtilis* strain and incubated for 48 hours at 28° C. was lyophilized, and 50% of the lyophilized dough powder was mixed with an equal amount of fresh masa flour, and made into dough. As a control, dough was made entirely from fresh masa flour. Both samples were placed in separate beakers, covered with foil, and incubated at 28° C. Observations were made for mold growth and off odors every day.

No mold growth was seen for the first three days in either sample. On the third day, the control dough was completely covered over with mold. The dough made out of a mixture of fresh masa flour and 50% lyophilized cultured dough, was totally free of mold. The dough also had a fresh odor and appearance (Table 9).

TABLE 9

Effect of adding lyophilized cultured dough powder to fresh masa flour on molding of masa dough during storage at 28° C.[a]

| Days at 28° C. | Control dough[b] Odor | Control dough[b] Mold | Experimental dough[c] Odor | Experimental dough[c] Mold |
|---|---|---|---|---|
| 0 | Normal | None | Normal | None |
| 1 | Normal | None | Normal | None |
| 2 | Sl. Off[d] | 2 spots | Normal | None |
| 4[e] | Off | +++++[f] | Normal | None |

[a]Masa dough inoculated with 1 × 10$^4$ *Bacillus subtilis*/gram of dough was incubated at 28° C. for 48 hours and lyophilized.
[b]Control dough was made from fresh masa flour.
[c]Experimental dough was made from a mixture of equal portions of fresh masa flour and lyophilized dough powder.
[d]Sl. Off - slightly off.
[e]No observations were made on the third day.
[f]+++++ - Entire surface of the dough was covered by mold.

This observation showed that cultured dough that has been dried is as effective as using moist dough. The culturing can be done on a thin suspension of dough, for example 5% to 10% in water, or even lower, using the *Bacillus subtilis* strain, and dried by lyophilization, or spray drying, or roller drying, or fluidized bed drying or by any other means available, and mixed with fresh masa flour at various proportions in the range of 5 to 50% or higher if necessary and used for various applications. Similar preparations can be used for various breads, baked goods and the like, where dough is the starting material. The *Bacillus subtilis* strain can be used for inhibiting molds, extending shelf-life, and preserving dough during handling or transportation to a separate baking site.

EXAMPLE 6

To examine if application of the *Bacillus subtilis* strain can be used to suppress molds and extend shelf-life in dairy products, shredded cheese was chosen as the test system.

Shredded Mozzarella cheese containing no added preservatives or antimicrobials, purchased from a local supermarket, was used for this application. The shredded cheese was taken out of the package, mixed uniformly on a plastic sheet using a clean spatula. The pooled cheese was then divided into four equal quarters, and 50 g portions were weighed out from each divided pool. Using a spray bottle, two of the portions were evenly sprayed with sterile dilution buffer (used for bacterial dilutions for counting), turning the cheese particles with a spatula to get an even spray. Approximately 15 minutes were allowed for the cheese to drain excess moisture. The two portions were then separately placed into two ZIPLOC bags, and sealed. The other two portions were similarly treated with $1 \times 10^{-4}$ dilution of the cell concentrate of the *Bacillus subtilis* strain made in the same dilution buffer. These portions were placed in two other ZIPLOC bags, and sealed. One each of the control and experimental bags were placed in a refrigerator held at 4° C., and the remaining bags were placed in an incubator set at 15° C. The cheeses were examined every day for the appearance of mold spots. The higher temperature was chosen to accelerate the growth of molds, and other deterioration of the cheese. No mold development was noticed in the samples held at 4° C. even after 2 weeks, and no deteriorative changes were found. No perceptible changes were seen on both samples stored at the higher temperature for the first 4 days. On the fifth day, the control sample stored at 15° C. had 3 spots of mold growth; the sample sprayed with cells, however, was completely free of molds. With the progression of storage at the higher temperature, the mold spots on the control samples got larger and began to taint the surrounding cheese particles. Mold spots on the sample treated with the culture spray appeared only after the 7th day (Table 10).

TABLE 10

Effect of spraying suspended cells of *Bacillus subtilis* on molding of shredded Mozzarella cheese stored at 15° C.[a]

| Days at | Control cheese | | Cheese sprayed with cell suspension | |
|---|---|---|---|---|
| 15° C. | Odor | Mold | Odor | Mold |
| 0 | Normal | None | Normal | None |
| 1 | Normal | None | Normal | None |
| 2 | Normal | None | Normal | None |
| 3 | Normal | None | Normal | None |
| 4 | Normal | None | Normal | None |
| 5 | Normal | 3 spots | Normal | None |

TABLE 10-continued

Effect of spraying suspended cells of *Bacillus subtilis* on molding of shredded Mozzarella cheese stored at 15° C.[a]

| Days at | Control cheese | | Cheese sprayed with cell suspension | |
|---|---|---|---|---|
| 15° C. | Odor | Mold | Odor | Mold |
| 6 | Normal | 3 spots | Normal | None |
| 7 | Off | 5 spots | Musty? | 3 spots |
| 8 | Off | 6 spots | Off | 5 spots |
| 9 | Off | 7 spots | Off | 5 spots |
| 12 | Moldy | ++++[b] | Off | 6 spots |

[a] Control cheese was evenly sprayed with sterile dilution buffer. Experimental cheese was evenly sprayed with a diluted culture concentrate of *Bacillus subtilis* containing $1.0 \times 10^5$ cfu/ml.
[b] Cheese particles tainted with mold extensively.

Based on the foregoing results, mold development, and deterioration in cheese can be retarded using the *Bacillus subtilis* strain. Similar methods can be used to control microbial deterioration in other dairy products including different cheeses, evaporated and condensed milks, creams, dairy spreads and the like.

EXAMPLE 7

The application of the *Bacillus subtilis* strain in packaging materials to suppress microflora of foods was examined. Tortillas were used as the test system.

Masa flour was converted to dough according to the instructions on the package to obtain approximately 300 g of dough. The dough was made into uniformly sized tortillas. Four ZIPLOC bags were turned inside out and the inner surface was uniformly sprayed with sterile dilution buffer using a spray-bottle. After the excess moisture had drained off, the bags were turned over so that the sprayed surface was on the inside. One tortilla was placed and sealed in each of the bags. Another set of ZIPLOC bags were sprayed with a suspension of *Bacillus subtilis* strain made in dilution buffer such that the suspension contained $1 \times 10^7$ CFU/ml. The bags were turned over and four tortillas were individually placed in these bags. All the bags were labeled for identity, sealed, and placed in a 28° C. incubator. The tortillas were daily examined for mold development. No mold development was seen on any the samples for the first four days. After the fifth day, three out of the four control tortillas (tortillas in bags sprayed with sterile dilution buffer) showed mold growth. One of the tainted tortillas had 5 spots of mold growth. Another one 4 mold spots, and the third one had one spot. Among the experimental tortillas (placed in bags sprayed with the *Bacillus subtilis* strain), only one showed two small spots of mold growth on the fifth day. By the sixth day molds in the infested control packages had spread to form large patches almost covering the entire surface of the tortillas. Three tortillas in the bags treated with *Bacillus subtilis* strain, in contrast were free of molds; the two spots of mold on the fourth tortilla in the experimental group remained confined to the same areas noted on the previous day. Treating the bags with a spray of the *Bacillus subtilis* strain definitely controlled mold development on the tortillas.

The *Bacillus subtilis* strain can thus be used to treat films, casings, and other packaging material to control mold growth on various food products like breads, cheeses, sausages, wieners, vegetables, fruits and the like.

In all the foregoing Examples, the *Bacillus subtilis* strain was found to be effective against mold development in various food systems. This strain can also be used to control molds in other food systems like dried fruits, vegetables, meats, fish and livestock feeds, silage and other forage crops.

It is intended that the foregoing description be only illustrative of the present invention and that the present invention be limited only by the hereinafter appended claims.

We claim:

1. A method for inhibiting undesirable microorganisms in a material containing or exposed to the microorganisms which comprises:

exposing the material to an inhibitor of the undesired microorganisms which is a biologically pure culture of a *Bacillus subtilis* deposited as NRRL B-21974 so that the undesired microorganisms in the material are inhibited.

2. The method of claim 1 wherein the material contains between $10^2$ and $10^9$ cfu of the *Bacillus subtilis* per gram of the material.

3. The method of claim 1 wherein the *Bacillus subtilis* is inoculated into the material as a concentrate containing between about $10^6$ and $10^{12}$ cfu per ml.

4. The method of claim 3 wherein the concentrate has been frozen and thawed prior to the inoculation.

5. The method of claim 3 wherein the concentrate has been dried and is inoculated into the food.

6. The method of any one of claims 1, 2 or 3 wherein the material is a food.

7. The method of any one of claims 1, 2 or 3 wherein the material is a packaging material for a food.

8. The method of claim 1 wherein the culture is living.

9. The method of claim 1 wherein the culture is non-living.

10. The method of claim 9 wherein the culture is disrupted.

11. A biologically pure culture of *Bacillus subtilis* deposited as NRRL B-21974.

12. The culture of claim 11 which is frozen with a preservative for storage of the culture as a live culture.

13. The culture of claim 11 which is lyophilized for preservation of the culture as a live culture.

14. The culture of claim 11 with a bulking agent.

15. The culture of claim 14 wherein the bulking agent is a dry flour.

16. The culture of claim 14 wherein the bulking agent is an edible powder.

* * * * *